(12) United States Patent
Lin (10) Patent No.: US 9,883,921 B2
(45) Date of Patent: Feb. 6, 2018

(54) CHANGEABLE POSITIONING DEVICE FOR DENTAL DRILLING

(71) Applicant: Hsieh-Hsing Lin, New Taipei (TW)

(72) Inventor: Hsieh-Hsing Lin, New Taipei (TW)

( * ) Notice: Subject to any disclaimer, the term of this patent is extended or adjusted under 35 U.S.C. 154(b) by 90 days.

(21) Appl. No.: 14/934,702

(22) Filed: Nov. 6, 2015

(65) Prior Publication Data

US 2017/0128155 A1     May 11, 2017

(51) Int. Cl.
*A61C 1/08*     (2006.01)

(52) U.S. Cl.
CPC ..................... *A61C 1/084* (2013.01)

(58) Field of Classification Search
CPC .......... A61C 1/082; A61C 1/084; A61C 1/085
See application file for complete search history.

(56) References Cited

U.S. PATENT DOCUMENTS

| | | | |
|---|---|---|---|
| 7,322,821 B1 * | 1/2008 | Lin | A61C 1/084 433/201.1 |
| 7,845,943 B2 * | 12/2010 | Meitner | A61C 1/084 433/75 |
| 8,523,566 B2 * | 9/2013 | Suter | A61C 1/084 433/72 |
| 2010/0297574 A1 * | 11/2010 | Llop | A61C 1/084 433/75 |
| 2014/0276879 A1 * | 9/2014 | Lin | A61B 17/1757 606/96 |

FOREIGN PATENT DOCUMENTS

FR          2896403     *   7/2007
WO     WO 2007/104842   *   9/2007

* cited by examiner

*Primary Examiner* — Ralph Lewis (57) ABSTRACT

A changeable positioning device for dental drilling comprises a base, a guide body and a positioning block. The base comprises a top end, a bottom end, a first outer wall, a first inner wall, a first guide groove, at least one first recess and at least one second recess. The at least one protrusion can be slidably fitted with the at least one first recess and the at least one second recess, thereby the second guide groove of the guide body will not be synchronously moved with a drill during drilling toward the axial direction of the guide body. The distance between the two extension portions is smaller than the diameter of the second inner wall at the same plane that is perpendicular to the axis of the guide body so that the drill will not deviate from the guide groove, thereby increasing the stability and precision of drilling.

7 Claims, 8 Drawing Sheets

CHANGEABLE POSITIONING DEVICE FOR DENTAL DRILLING

BACKGROUND OF THE INVENTION

1. Field of the Invention

The present invention relates to a positioning device, particularly to a changeable positioning device for dental drilling.

2. Description of the Prior Arts

Teeth are calcified structure formed in the mouth for biting and chewing. An adult's teeth may be damaged by oral diseases or external forces, and the broken teeth are unable to regenerate. After the teeth are damaged, the alveolar bone and the gums of the mouth may be shrunk, and this may impair the eating capability. To avoid the above-mentioned problem, the common treatment is dental implant to replace the broken or lost teeth with denture.

When a patient's tooth is broken or missing, a common treatment is to replace the tooth with a denture. A common method of a denture implant is fixed tooth implant. The fixed tooth implant is processed by first drilling a socket at an appropriate position where a tooth is missing on an alveolar bone in a patient's mouth, and then an artificial implant fixture is implanted into the socket. The socket is sutured after implantation of the artificial implant fixture. When the artificial implant fixture grows fully integrated with the alveolar bone, an abutment having a screw is mounted on the artificial implant fixture. The denture is mounted on the abutment and fully sustained on the alveolar bone by the abutment and the artificial implant fixture, so the denture can bear the biting force thus to restore the biting function of the patient's teeth.

Figure 8:
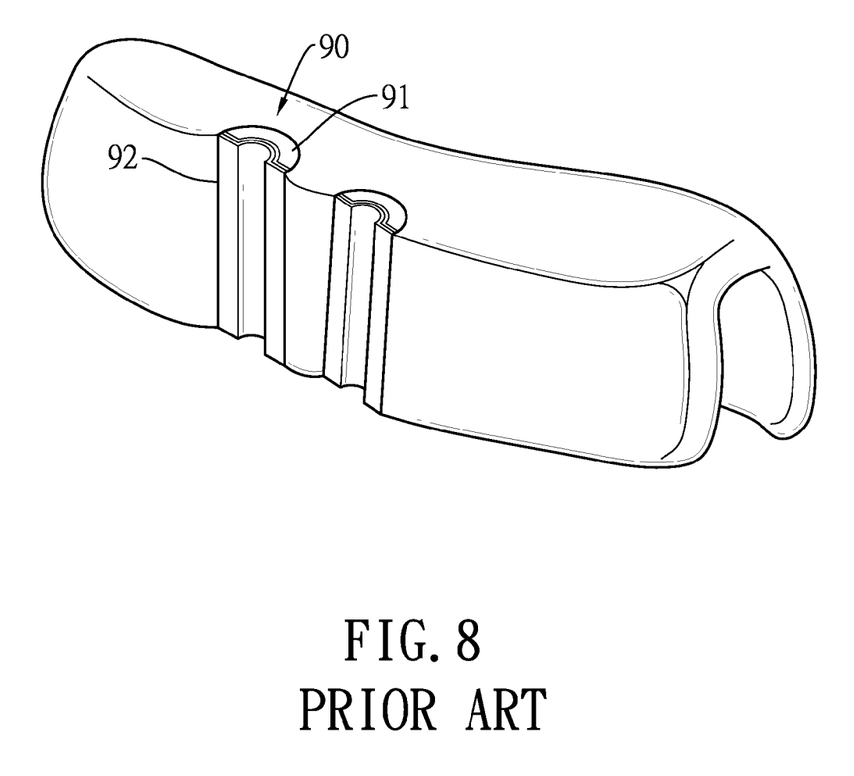
FIG. 8 is a perspective view of the drilling positioning auxiliary device for tooth implantations of the prior art and the surgical guide.

Taiwan patent number M498344, which is incorporated herein as a reference as shown in FIG. 8, discloses a drilling positioning auxiliary device for tooth implantations comprising a positioning device 90 formed in a hollow semi-cylinder. The positioning device 90 is embedded in a surgical guide in order to facilitate a drill's drilling in the alveolar bone. The positioning device 90 comprises a base body 91 and at least one guide portion 92 abutting the base body 91, and increases or decreases the number of the at least one guide portion 92 to adjust the size of the socket drilled. Although the semi-cylinder design allows the drill to be easily placed into the positioning device 90 in the limited oral space, the design also increases the instability of drilling, and the drill may be displaced due to lack of a supporting wall. Besides, the at least one guide portion 92 does not tightly connect with the base body 91 when the drill is drilling toward the axial direction of the base body 91 and the at least one guide portion 92 is synchronously moved with the drill, thereby causing great disturbance during operation.

Therefore, to develop stable drilling for the drill and stably combining the guide body and the positioning device, the disadvantages in the prior arts should be resolved.

SUMMARY OF THE INVENTION

According to the above description, the objective of the present invention is to provide a changeable positioning device for dental drilling for stably combining the guide body and supporting the drill during drilling.

The objective of the invention is to provide a changeable positioning device for dental drilling, comprising a base, a guide body and a positioning block. The base comprises a top end, a bottom end, a first outer wall, a first inner wall, a first guide groove, at least one first recess, and at least one second recess. The top end is located at one end of an axial direction of the base. The bottom end is opposite to the top end. The first outer wall is located at an outer surface of the base and between the top end and the bottom end. The first inner wall is opposite to the first outer wall and comprises two edges and an opening; the two edges are between the top end and the bottom end and are parallel to the axial direction of the base; the opening is between the two edges. The first guide groove is surrounded by the first inner wall and is connected to and communicates with the opening of the first inner wall. The at least one first recess is recessed to the first inner wall and comprises a first notch and a first abutment surface; the first notch is formed from the at least one first recess along the axial direction of the base through the top end; the first abutment surface is opposite to the first notch. The at least one second recess is recessed from the first inner wall and recessed from the at least one first recess distal from the opening; the at least one second recess is connected to and communicates with the at least one first recess, and an axial length of the at least one second recess is shorter than an axial length of the at least one first recess. The guide body comprises a second outer wall, a second inner wall, a second guide groove, two extension portions, and at least one protrusion. The second outer wall is detachably attached with the first inner wall of the base; the second inner wall is opposite to the second outer wall; the second guide groove is surrounded by the second inner wall; the two extension portions extend respectively from ends of the second outer wall and of the second inner wall, an axial direction of each of the two extension portions is parallel to the axial direction of the base; the at least one protrusion protrudes respectively from the second outer wall and is detachably engaged in the at least one first recess of the base. The positioning block protrudes from the first outer wall of the base.

Preferably, the base and the guide body are each formed as a hollow semi-cylinder.

More preferably, a distance between the two extension portions is shorter than a diameter of the second inner wall.

Preferably, the positioning block has two opposite sides, and one of the sides is connected to the first outer wall of the base; a width of the positioning block perpendicular to a cross-sectional plane in the axial direction of the base is gradually reduced from one of the sides of the positioning block distal from the first outer wall to the other side of the positioning block connecting to the first outer wall.

Preferably, the base further comprises a slot recessed from the top end toward the bottom end, and the slot is adjacent to the top end and opposite to the opening.

Preferably, an axial height of the at least one protrusion and the axial length of the at least one second recess are equal, and the axial height of the at least one protrusion is shorter than the axial length of the at least one first recess.

Preferably, the at least one second recess comprises a second notch and a second abutment surface; the second notch is formed from the at least one second recess along the axial direction of the base through the bottom end; a second abutment surface is opposite to the second notch.

More preferably, an axial height of the at least one protrusion and a distance between the first abutment surface of the first recess and the second abutment surface of the second recess are equal.

Preferably, the base further comprises two opposite bulges; the bulges protrude from the first outer wall, are located near the two edges of the first inner wall, and extend away from each other.

More preferably, the bulges are formed as slices or pillars, and the bulges are adjacent to the top end of the base.

Preferably, the at least one first recess of the base is implemented as two opposite first recesses, the at least one second recess of the base is implemented as two opposite second recesses, and the at least one protrusion of the guide body is implemented as two opposite protrusions; each of the protrusions and each of the first recesses of the base, or each of the protrusions and each of the second recesses of the base can be detachably engaged.

The advantages of the present invention are:

1. The at least one protrusion of the guide body can be slidably fitted with the at least one first recess and the at least one second recess of the base, such that the second guide groove of the guide body will not be synchronously moved with a drill during drilling toward the axial direction of the guide body.

2. The distance between the two extension portions is smaller than the diameter of the second inner wall at the same plane that is perpendicular to the axis of the guide body so that the drill will not deviate from the guide groove, thereby increasing the stability and precision of drilling.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
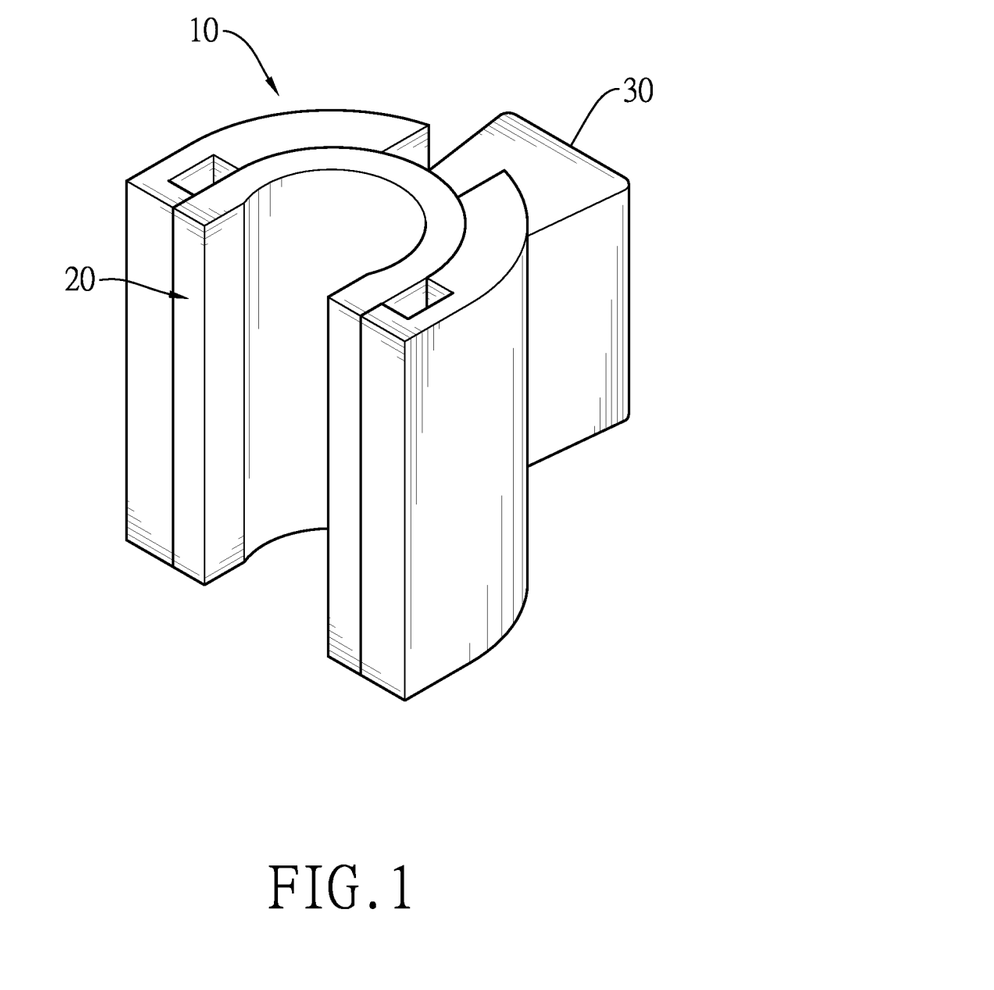
FIG. 1 is a perspective view of a first preferred embodiment of the changeable positioning device for dental drilling of the present invention.

As shown in FIG. 1, the first preferred embodiment of the present invention provides a changeable positioning device for dental drilling comprising a base 10, a guide body 20 and a positioning block 30.

Figure 2:
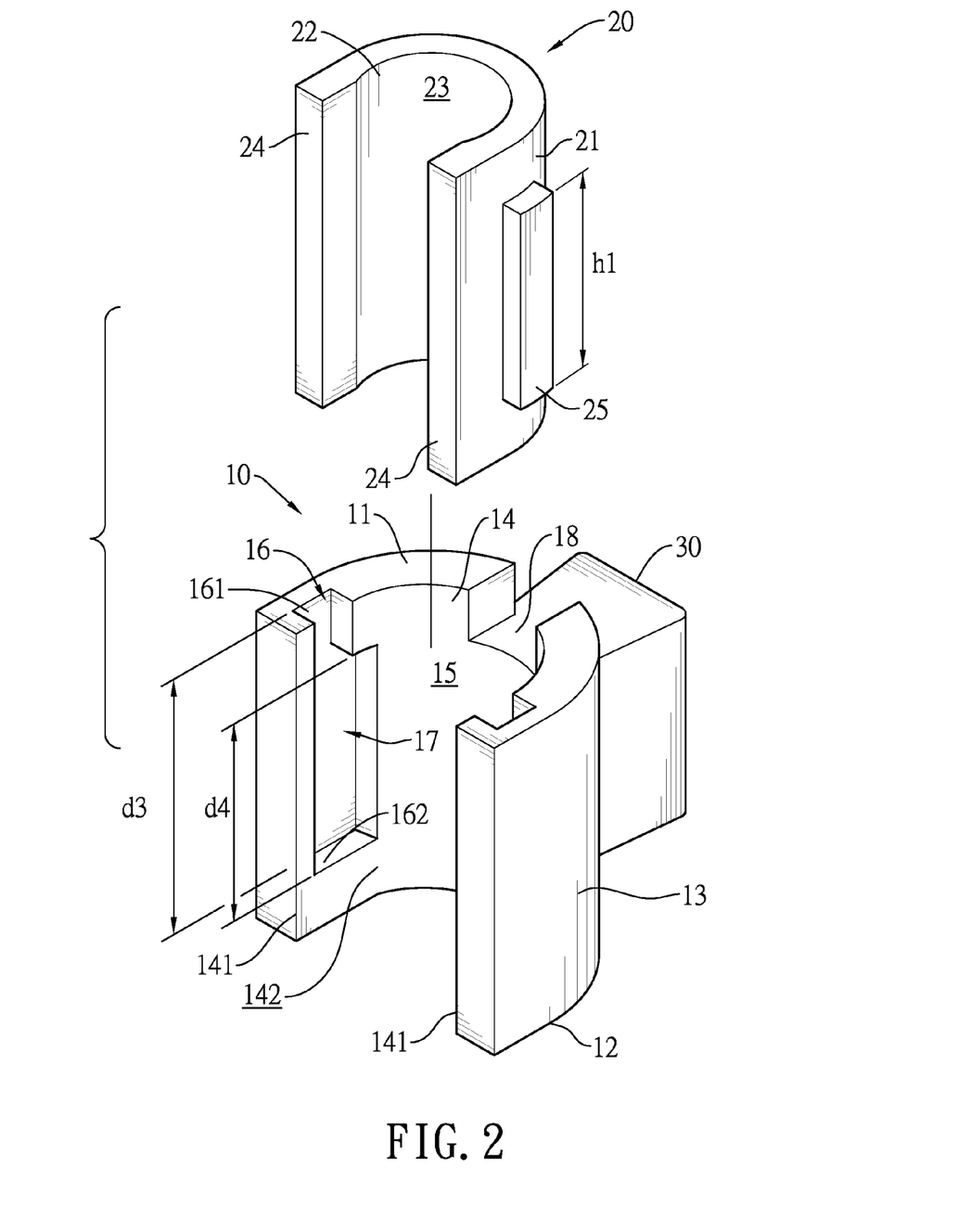
FIG. 2 is an exploded view of the first preferred embodiment of the changeable positioning device for dental drilling of the present invention.
Figure 3:
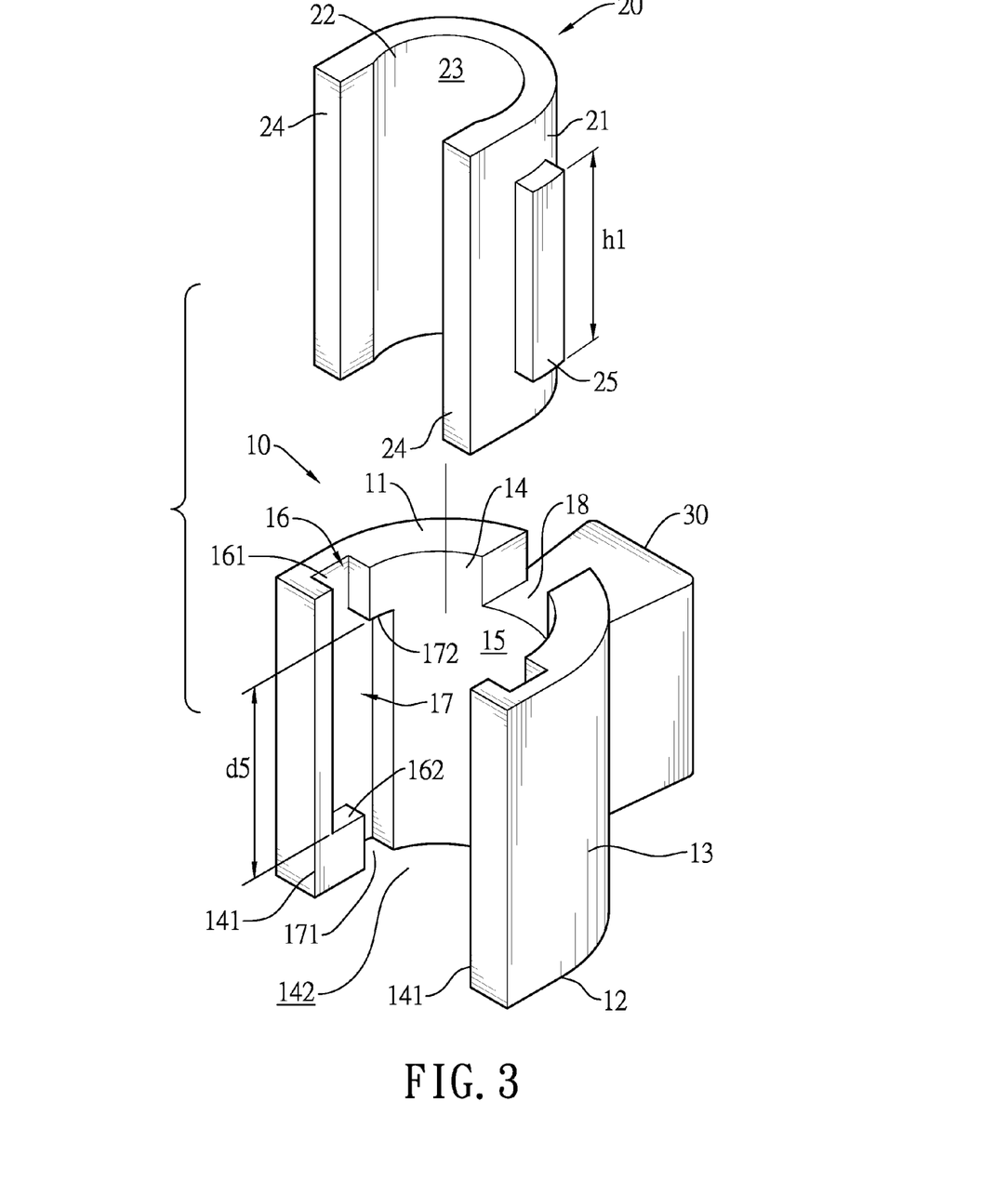
FIG. 3 is another exploded view of the first preferred embodiment of the changeable positioning device for dental drilling of the present invention.

As shown in FIG. 2, the base 10 is formed as hollow semi-cylinder and comprises a top end 11, a bottom end 12, a first outer wall 13, a first inner wall 14, a first guide groove 15, at least one first recess 16, at least one second recess 17 and a slot 18. The top end 11 is located at one end of an axial direction of the base 10. The bottom end 12 is opposite to the top end 11. The first outer wall 13 is located at an outer surface of the base 10, and the first outer wall 13 is between the top end 11 and the bottom end 12. The first inner wall 14 is opposite to the first outer wall 13 and comprises two edges 141 and an opening 142; the two edges 141 are between the top end 11 and the bottom end 12, and the two edges 141 are parallel to the axial direction of the base 10; the opening 142 is between the two edges 141. The first guide groove 15 is surrounded by the first inner wall 14 and is connected to and communicates with the opening 142 of the first inner wall 14. The at least one first recess 16 is recessed to the first inner wall 14 and comprises a first notch 161 and a first abutment surface 162; the first notch 161 is formed from the at least one first recess 16 along the axial direction of the base 10 through the top end 11; the first abutment surface 162 is opposite to the first notch 161. The at least one second recess 17 is recessed from the first inner wall 14 and recessed from the at least one first recess 16 distal from the opening 142; the at least one second recess 17 is connected to and communicates with the at least one first recess 16, and an axial length d4 of the at least one second recess 17 is shorter than an axial length d3 of the at least one first recess 16. As shown in FIG. 3, in a preferred embodiment, the at least one second recess 17 comprises a second notch 171 and a second abutment surface 172; the second notch 171 is formed from the at least one second recess 17 along the axial direction of the base 10 through the bottom end 12; the second abutment surface 172 is opposite to the second notch 171. In a preferred embodiment, the at least one first recess 16 of the base 10 is implemented as two opposite first recesses 16, and the at least one second recess 17 of the base 10 is implemented as two opposite second recesses 17. The slot 18 is recessed from the top end 11 toward the bottom end 12 and is adjacent to the top end 11 and opposite to the opening 142.

Figure 4:
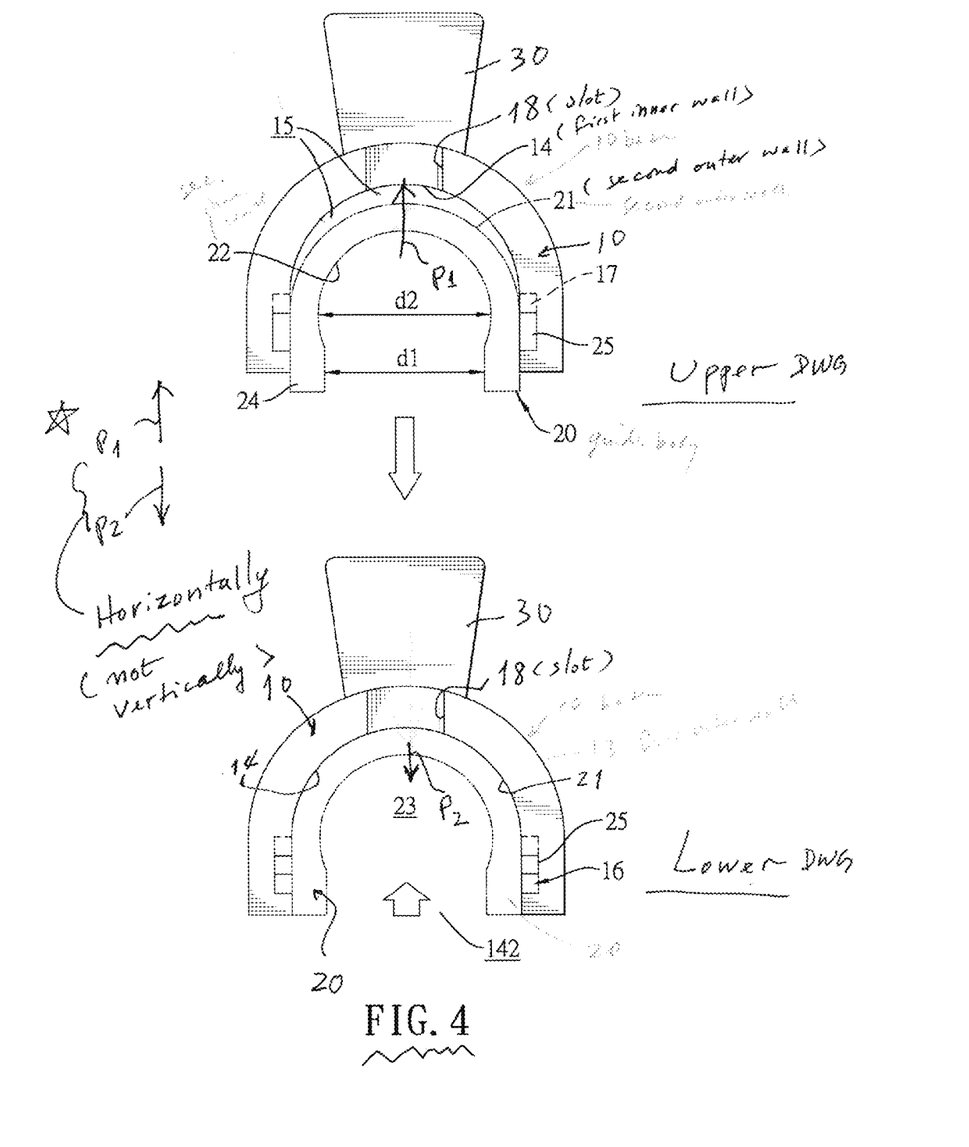
FIG. 4 is a cross-sectional view and plane view of the first preferred embodiment of the changeable positioning device for dental drilling of the present invention.

As shown in FIG. 2 and FIG. 4, the guide body 20 formed as a hollow semi-cylinder comprises a second outer wall 21, a second inner wall 22, a second guide groove 23, two extension portions 24 and at least one protrusion 25. The second outer wall 21 is detachably attached with the first inner wall 14 of the base 10. The second inner wall 22 is opposite to the second outer wall 21. The second guide groove 23 is surrounded by the second inner wall 22. The two extension portions 24 extend respectively from ends of the second outer wall 21 and of the second inner wall 22, and an axial direction of each of the two extension portions 24 is parallel to the axial direction of the base 10. A distance d1 between the two extension portions 24 is shorter than a diameter d2 of the second inner wall 22. The at least one protrusion 25 protrudes from the second outer wall 21 and is detachably engaged in the at least one first recess 16 of the base 10. An axial height h1 of the at least one protrusion 25 and the axial length d4 of the at least one second recess 17 are equal, and the axial height h1 of the at least one protrusion 25 is shorter than the axial length d3 of the at least first recess 16. As shown in FIG. 3 and FIG. 4, in a preferred embodiment, the axial height h1 of the at least one protrusion 25 and a distance d5 between the first abutment surface 162 of the first recess 16 and the second abutment surface 172 of the second recess 17 are equal. In a preferred embodiment, the at least one first recess 16 of the base 10 is implemented as two opposite first recesses 16, the at least one second recess 17 of the base 10 is implemented as two opposite second recesses 17, and the at least one protrusion 25 is implemented as two opposite protrusions 25; each of the protrusions 25 and each of the first recesses 16 of the base 10, or each of the protrusions 25 and each of the second recesses 17 of the base 10 can be detachably engaged.

The positioning block 30 protrudes from the first outer wall 13 of the base 10 and has two opposite sides, including a first side connected to the first outer wall 13 of the base 10 and a second side protruding outwardly from the first side to be distally opposite to the first side; a width of the positioning block 30 perpendicular to a cross-sectional plane in the axial direction of the base 10 gradually reduced from the second side of the positioning block 30 distal from the first outer wall 13 to the first side of the positioning block 30 connected to the first outer wall 13. As shown in FIG. 4, the plane view of the positioning block 30 is in a dovetail shape.

Figure 5:
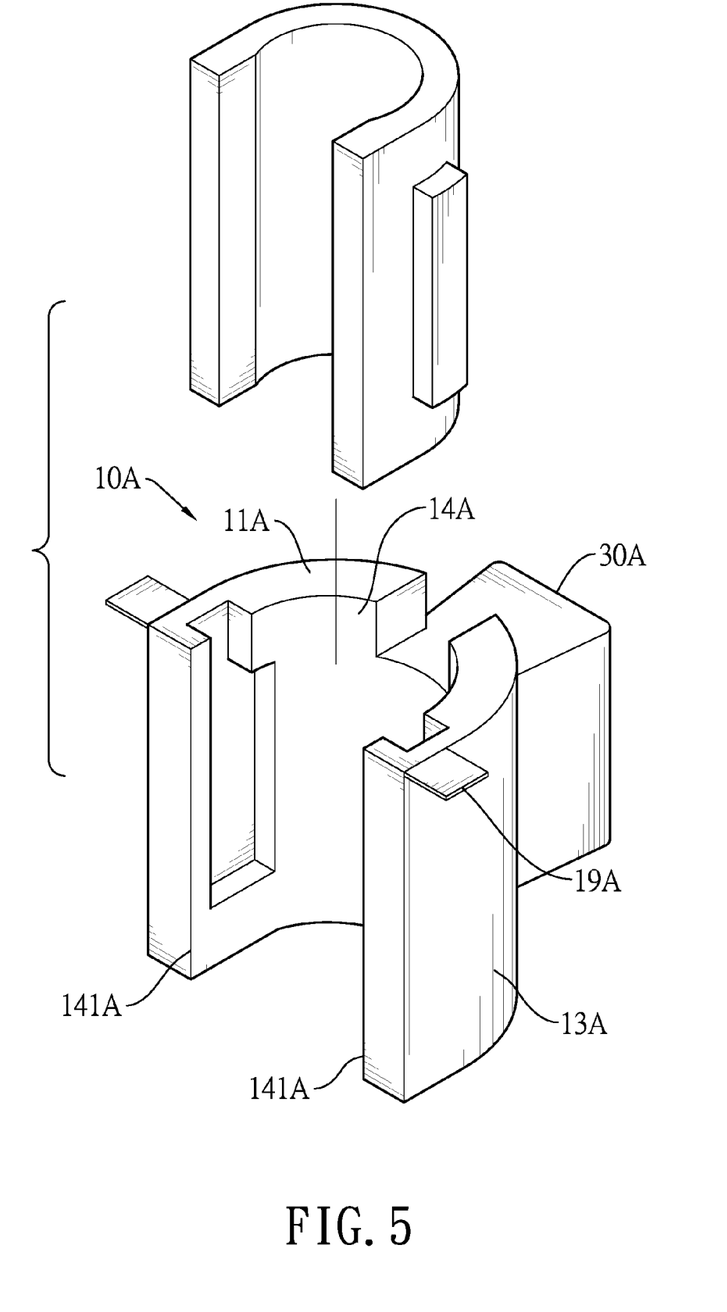
FIG. 5 is an exploded view of a second preferred embodiment of the changeable positioning device for dental drilling of the present invention.

As shown in FIG. 5, the difference between the second preferred embodiment and the first preferred embodiment of the present invention is that the base 10A further comprises two opposite bulges 19A. The bulges 19A protrude from the first outer wall 13A and are located near the two edges 141A of the first inner wall 14A, and the bulges 19A extend away from each other. In a preferred embodiment, the bulges 19A are formed as slices or pillars, and the bulges 19A are adjacent to the top end 11A of the base 10A.

As shown in FIG. 2 and FIG. 4, when the first preferred embodiment of the present invention is in use, the base 10 and the positioning block 30 of the changeable positioning device for dental drilling are embedded into a surgical guide simulating a patient's teeth, and then each of the two protrusions 25 of the guide body 20 is respectively inserted into each of the two first notches 161 of the first recesses 16 of the base 10. When each of the protrusions 25 abuts on each of the first abutment surfaces 162, each of the protrusions 25 is further inserted into each of the second recesses 17 so that the second outer wall 21 are attached with the first inner wall 14 of the base 10. Each of the protrusions 25 of the guide body 20 can be slidably fitted with each of the first recesses 16 and each of the second recesses 17 of the base 10, thereby the second guide groove 23 of the guide body 20 will not be synchronously moved with a drill during drilling toward the axial direction of the guide body 20. When the guide body 20 is to be changed to another guide body 20 having a second inner wall 22 of a different diameter d2, the second outer wall 21 of the guide body 20 is pushed through the slot 18 of the base 10 so that the guide body 20 will be moved from the second recess 17 to the first recess 16, and the second outer wall 21 is distal from the first inner wall 14. Then, each of the protrusions 25 is pulled toward each of the first notches 161, and another guide body 20 inserted into the base 10 is followed with the same steps to finish the changing.

Figure 6:
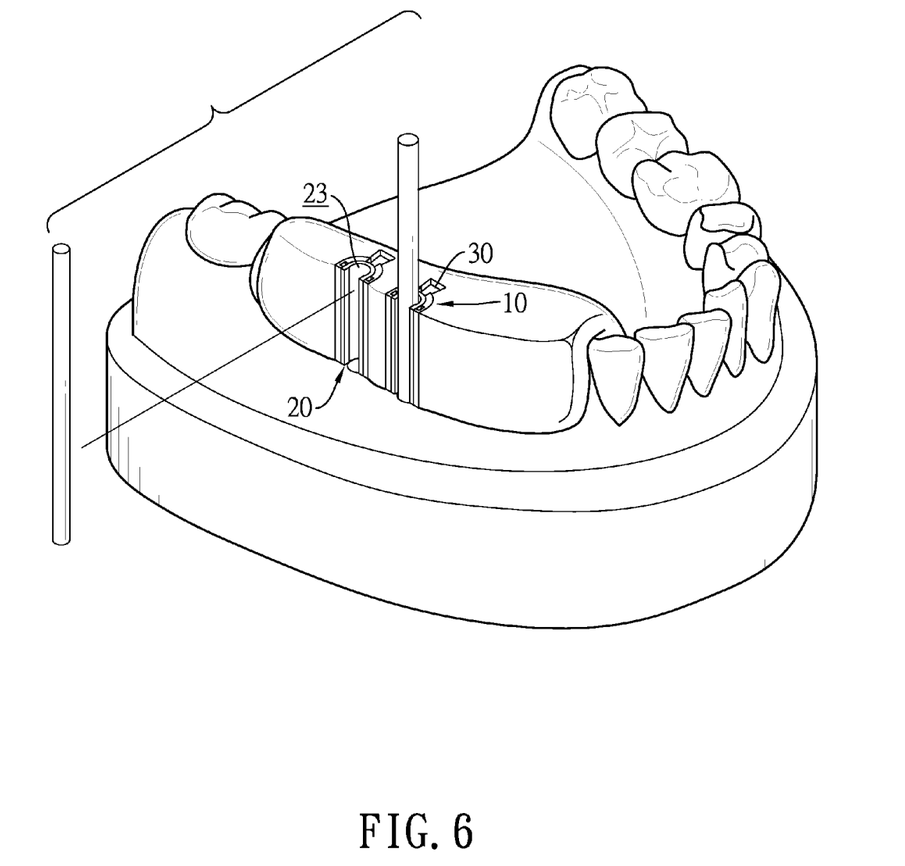
FIG. 6 shows an operational view of the first preferred embodiment of the changeable positioning device for dental drilling of the present invention and the surgical guide.

As shown in FIG. 4 and FIG. 6, the drill goes through a space between the two extension portions 24 of the guide body 20 into the second guide groove 23, and then the drill is drilling along the second guide groove 23 toward the axial direction of the guide body 20. Because the distance d1 between the two extension portions 24 is smaller than the diameter d2 of the second inner wall 22, the drill can be easily inserted into the second guide groove 23 in the limited oral space, and the drill will not deviate from the second guide groove 23 or toward to the extension portions 24, thereby increasing the stability and precision of drilling.

Figure 7:
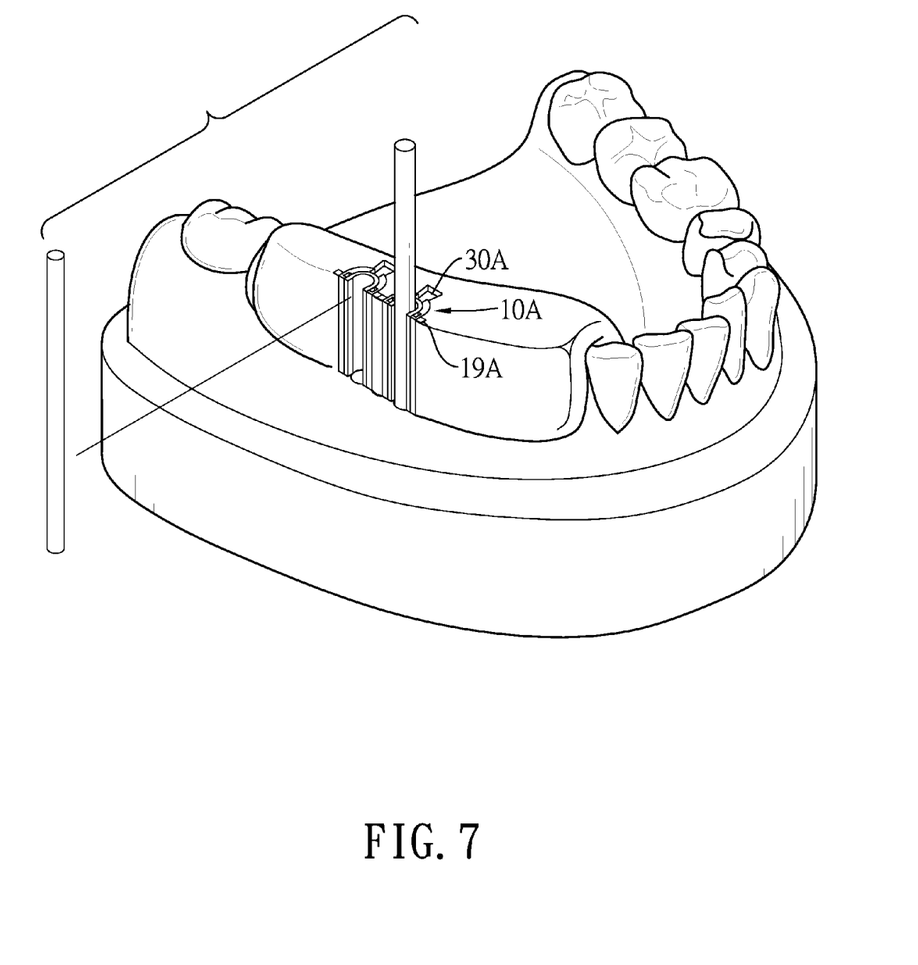
FIG. 7 shows an operational view of the second preferred embodiment of the changeable positioning device for dental drilling of the present invention and the surgical guide.

As shown in FIG. 5 and FIG. 7, when the second preferred embodiment of the present invention is in use, the base 10A and the positioning block 30A of the changeable positioning device for dental drilling of the present invention are embedded into a surgical guide simulating a patient's teeth. When two adjacent teeth need to be implanted, two appropriate lengths of the bulges 19A are selected after calculating a distance between the teeth. The two adjacent bulges 19A of the base 10A are connected to each other by an end away from the first outer wall 13A of each of the bulges 19A, and then the positioning device for dental drilling is embedded in the surgical guide to reduce required times of measurements and increase the efficiency of fabrication.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A changeable positioning device for dental drilling, comprising:
   a base, comprising:
   a top end located at one end of an axial direction of the base;
   a bottom end opposite to the top end;
   a first outer wall located at an outer surface of the base, and the first outer wall being between the top end and the bottom end;
   a first inner wall opposite to the first outer wall, comprising:
   two edges between the top end and the bottom end and parallel to the axial direction of the base; and
   an opening between the two edges;
   a first guide groove surrounded by the first inner wall, and the first guide groove connected to and communicating with the opening of the first inner wall;
   at least one first recess recessed to the first inner wall, and the at least one first recess comprising:
   a first notch formed from the at least one first recess along the axial direction of the base through the top end; and
   a first abutment surface opposite to the first notch; and
   at least one second recess recessed from the first inner wall, and the at least one second recess recessed from the at least one first recess distal from the opening; the at least one second recess connected to and communicating with the at least one first recess, and an axial length of the at least one second recess being shorter than an axial length of the at least one first recess; and
   a guide body, comprising:
   a second outer wall detachably attached with the first inner wall of the base;
   a second inner wall opposite to the second outer wall;
   a second guide groove surrounded by the second inner wall;
   two extension portions extending respectively from ends of the second outer wall and of the second inner wall, an axial direction of the each of the two extension portions being parallel to the axial direction of the base; and
   at least one protrusion protruding from the second outer wall, and the at least one protrusion detachably engaged in the at least one first recess of the base; and
   a positioning block having two opposite sides, including a first side connected to the first outer wall of the base; and a second side protruding outwardly from said first side to be distally opposite to said first side; a width of the positioning block being perpendicular to a cross-sectional plane in the axial direction of the base and gradually reduced from said second side of the positioning block to the first side of the positioning block connected to the first outer wall to define a dovetail shape of the positioning block;

an axial height of the at least one protrusion and the axial length of the at least one second recess being equal, and the axial height of the at least one protrusion being shorter than the axial length of the at least one first recess.

2. The changeable positioning device for dental drilling as claimed in claim 1, wherein the base and the guide body are each formed as a hollow semi-cylinder.

3. The changeable positioning device for dental drilling as claimed in claim 2, wherein a distance between two extension portions of said guide body is shorter than a diameter of a second inner wall opposite to a second outer wall of said guide body.

4. The changeable positioning device for dental drilling as claimed in claim 1, wherein the base further comprises a slot recessed from the top end toward the bottom end, and the slot is adjacent to the top end and opposite to the opening.

5. The changeable positioning device for dental drilling as claimed in claim 1, wherein the at least one second recess recessed from the at least one first recess comprises:

a second notch formed from the at least one second recess along the axial direction of the base through the bottom end; and a second abutment surface opposite to the second notch; and an axial height of the at least one protrusion and a distance between said first abutment surface of the first recess and the second abutment surface of the second recess being equal.

6. The changeable positioning device for dental drilling as claimed in claim 1 wherein the base further comprises two opposite bulges; the bulges protrude from the first outer wall, are located near the two edges of the first inner wall, and extend away from each other.

7. The changeable positioning device for dental drilling as claimed in claim 1, wherein the at least one first recess of the base is implemented as two opposite first recesses, the at least one second recess of the base is implemented as two opposite second recesses, and the at least one protrusion of the guide body is implemented as two opposite protrusions; each of the protrusions and each of the first recesses of the base, or each of the protrusions and each of the second recesses of the base are detachably engaged.

* * * * *